US007308127B2

(12) United States Patent
Bernatek et al.

(10) Patent No.: US 7,308,127 B2
(45) Date of Patent: Dec. 11, 2007

(54) METHOD FOR DETERMINING AND EVALUATING DEFECTS IN A SAMPLE SURFACE

(75) Inventors: Christian Bernatek, Rodgau (DE); Frank Kellner, Bad Hersfeld (DE); Peter March, Frankfurt (DE)

(73) Assignee: Atlas Material Testing Technology GmbH, Linsengericht-Altenhablau (DE)

( * ) Notice: Subject to any disclaimer, the term of this patent is extended or adjusted under 35 U.S.C. 154(b) by 875 days.

(21) Appl. No.: 10/466,694

(22) PCT Filed: Dec. 12, 2001

(86) PCT No.: PCT/DE01/04715

§ 371 (c)(1),
(2), (4) Date: Jul. 21, 2003

(87) PCT Pub. No.: WO02/057761

PCT Pub. Date: Jul. 25, 2002

(65) Prior Publication Data

US 2004/0081347 A1    Apr. 29, 2004

(30) Foreign Application Priority Data

Jan. 19, 2001  (DE) ................................ 101 02 387

(51) Int. Cl.
*G06K 9/00* (2006.01)
*G01N 21/00* (2006.01)
*G09G 5/00* (2006.01)

(52) U.S. Cl. .................... 382/141; 356/237.2; 345/626

(58) Field of Classification Search ................ 382/141; 356/237.2; 345/626; 118/323
See application file for complete search history.

(56) References Cited

U.S. PATENT DOCUMENTS

| 4,629,319 | A | * | 12/1986 | Clarke et al. ............ 356/237.2 |
| 4,861,164 | A | * | 8/1989 | West .......................... 356/445 |
| 4,868,404 | A | * | 9/1989 | Hajime ................... 250/559.22 |
| 4,895,446 | A | * | 1/1990 | Maldari et al. ............. 356/336 |
| 5,155,558 | A | * | 10/1992 | Tannenbaum et al. ...... 356/446 |
| 5,576,829 | A | * | 11/1996 | Shiraishi et al. ............ 356/521 |

(Continued)

FOREIGN PATENT DOCUMENTS

DE  41 21 464 A1   1/1992

(Continued)

OTHER PUBLICATIONS

Oishi Hiroyuki et al., Patent Abstracts of Japan, "Defective Painting Inspection System", Aug. 23, 1994.

*Primary Examiner*—Matthew C. Bella
*Assistant Examiner*—Utpal Shah
(74) *Attorney, Agent, or Firm*—Vedder Price Kaufman and Kammholz

(57) ABSTRACT

In this method, the surface to be investigated is first of all exposed to collimated light and the radiation rejected therefrom supplied to a position-resolving image processing means. Then, a mask is generated on the basis of the image supplied by the image processing means, said mask having masked regions being defined by relatively bright areas of said image and unmasked regions being defined by relatively dark areas of said image. Now, the surface to be investigated is exposed to diffuse light and the radiation rejected therefrom supplied to the image processing means, with only the radiation from the unmasked regions being taken into consideration for analyzing purposes.

9 Claims, 4 Drawing Sheets

U.S. PATENT DOCUMENTS

| | | | |
|---|---|---|---|
| 5,726,705 A * | 3/1998 | Imanishi et al. | 348/92 |
| 5,828,500 A * | 10/1998 | Kida et al. | 359/798 |
| 5,831,725 A | 11/1998 | Lee | |
| 6,020,954 A * | 2/2000 | Aggarwal | 356/30 |
| 6,061,125 A * | 5/2000 | Thomas et al. | 356/237.1 |
| 6,148,097 A | 11/2000 | Nakayama et al. | |
| 6,198,529 B1 * | 3/2001 | Clark et al. | 356/237.5 |
| 6,201,600 B1 * | 3/2001 | Sites et al. | 356/124 |
| 6,266,138 B1 * | 7/2001 | Keshavmurthy | 356/237.2 |
| 6,630,996 B2 * | 10/2003 | Rao et al. | 356/237.5 |
| 6,847,443 B1 * | 1/2005 | Herod et al. | 356/237.2 |

FOREIGN PATENT DOCUMENTS

| | | |
|---|---|---|
| DE | 41 39 107 C1 | 7/1993 |
| JP | 06-034349 | 2/1994 |
| JP | 07063530 | 3/1995 |
| JP | 07-159142 | 6/1995 |
| JP | 07159142 | 6/1995 |
| JP | 09-015165 | 1/1997 |
| JP | 09015165 | 1/1997 |
| JP | 09-105618 | 4/1997 |
| WO | WO98/16815 | 4/1998 |

* cited by examiner

METHOD FOR DETERMINING AND EVALUATING DEFECTS IN A SAMPLE SURFACE

The invention refers to an optical image recognition method used to detect and analyze defects of a sample surface such as the varnish surface of a vehicle. Particularly, the invention relates to a method in which the sample surfaces to be investigated are successively illuminated with two different kinds of light and then analyzed.

Optical image recognition methods are an important factor when surfaces, such as varnish surfaces of vehicles, are investigated which were exposed, for example, to either natural or artificial weathering conditions and when the surface defects caused by such weathering are detected and analyzed.

The quality checks of these paint coatings particularly also refer to the adhesive resistance thereof with regard to stone impacts. To do so, the automotive industry usually provides plane samples of metal sheet with paint coatings and bombards them with stone or metal splinters. Any defects thereby caused in the sample paint coatings will then be analyzed and classified. This method is a substantial component in quality grading of paint coatings.

Vehicle paint coatings often have a structure in which an electrocoat layer, a filler coat layer, the actual paint coat layer and finally a transparent coat layer are successively applied to the metal body. Such exterior influences as described above may cause defects of different kind to such coating structure, e.g. scratches, perforations or deformations. Those defects caused by removal of material particularly differ from each other in their dimensions of depth, such demolition taking place either at boundary faces between adjacent coat layers as well as within individual coat layers. To get information about the durability of the materials used for the structure of the coat layers or on the adhesion between the coat layers it is important to detect the microstructure of such defects and the frequency ratio of different structural features of the defect.

To do so, diverse optical image recognition methods have been developed which have in common that the surface of the piece of material to be investigated is illuminated under reproducible conditions and the light rejected from said surface is supplied to an image processing means to produce an image of the paint coating defects.

DE-PS 41 39 107 C1 reveals a method for detecting and analyzing changes in the surfaces of samples exposed to either artificial or natural weathering conditions. Images of the sample surface are taken, digitized and stored in a computer which generates gray level histograms of said images by an illuminating means and an electronic camera including a position-resolving detector. Then, the surface changes can be detected by subtraction of the gray level histograms of a sample not exposed to weathering conditions or a standard reference field and the sample exposed to weathering conditions. It is, however, not yet possible to detect the defects occurring at different depths of a paint coating structure and to differentiate them from each other by said method.

WO 98/16815 describes a means to investigate surface defects, said means comprising a first light source used to generate in a first step collimated light by means of suitable optical elements and to direct it to a sample surface to be investigated. The light is rejected by the sample surface and directed to a position-resolving detector such as a CCD detector of an image processing means by which taken pictures can be stored. Further, another light source is provided used to generate diffuse light by means of a suitable optical means and to direct it, in another step, to the sample surface. The light rejected by the sample surface is also supplied to the image processing means by which corresponding images can be stored. To use said two kinds of light and to compare the steps performed therewith allows that the detected defects can be characterized. For example, said method enables to detect and identify defects occurring in the outer transparent coat layer of vehicle paint coatings as well as defects occurring in the paint coating below said transparent coat layer. Accordingly, WO 98/16815, in particular the means described in FIG. 1 in combination with the appertaining description used to generate the two kinds of collimated and of diffuse light, is hereby included into the disclosure of the present application.

In particular, the above-mentioned reference does not describe any measures to be taken to illuminate the sample, to take the picture, and to analyze the image data obtained, respectively, in order to take a picture of optimum contrast. In this connection it is a decisive factor that, on the one hand, transparent coat layers are used and that, on the other hand, the color differences in the other paint coatings may be of minor kind which might render any recognition more difficult.

Up to now, however, there has been no publication found indicating how the efficiency of the method described in WO 98/16815 might be fully exhausted.

Thus, it is the object of the invention to provide a method to detect and analyze defects occurring in a sample surface by which defects can be detected and assigned unerringly and with utmost precision. In particular, such method can be used to give statements on the structure and the dimension of depth of defects.

This object is solved by the features of claim 1. Further advantageous developments are included in the sub-claims.

Accordingly, the present invention describes a method to detect and analyze defects occurring in a sample surface, wherein the sample surface to be investigated is successively illuminated with two kinds of light and images of the surface are taken and analyzed on the basis of the rejected radiation by means of an image processing means.

It is, thus, a principal idea of the invention to use the results obtained by analyzing the first illumination step performed with collimated light to execute the second illumination step with diffuse light under improved illumination conditions.

First of all, the surface to be investigated is illuminated with collimated light and the radiation rejected therefrom supplied to a position-resolving image processing means. Now, a mask is generated on the basis of the image supplied by the image processing means, the masked regions thereof being defined by areas of relative brightness and the unmasked regions being defined by areas of relative darkness of said image. Then, the surface to be investigated is illuminated with diffuse light and the radiation rejected therefrom is supplied to the image processing means, with only the radiation coming from the unmasked areas being taken into consideration for setting the illumination conditions.

Owing to this procedure, it is possible to set optimum illumination conditions in said second method step, since, due to the effect of the mask, just the portion of backscattered diffuse light originating from the defects is taken into consideration to set the illumination conditions. Thus, the portion of backscattered light originating from the sample surface areas that have no defects is left out of consideration and those defects that must by all means be investigated can be illuminated optimally.

The first illuminating step with collimated, preferably parallel (direct) light is, thus, first of all used to make all plane surface deviations visible, i.e. also all paint coating defects, irrespective of the question whether the coat layers concerned are transparent, opaque or absolutely non-transparent. Such deviations, of what kind ever they are, appear on the exposure of a picture taken with collimated light as dark areas, since the light occurring at the deviations is no more reflected to the image processing means as in case of the regions without defects. Said regions without defects appear in turn as bright areas, since the direct light is reflected to the image processing means.

First of all, collimated light is used to set optimum illumination conditions. Then, the image processing means generates an image. Now, a mask is generated in which the masked regions are generated by the bright image areas without defects and the unmasked regions are generated by the dark defective image areas. For the subsequently following illuminating step performed with diffuse light, said mask is used to set optimum illuminating conditions. For such setting, the bright areas without defects are advantageously left out of consideration which might otherwise cause an undesired overlaying of the defective areas. The defective areas could no longer be illuminated optimally.

In a preferred embodiment, gray level histograms of the taken images are generated in the respective illuminating steps. Said histograms can especially be used to set the optimum illuminating conditions which are given if the gray level values of the taken image are of utmost broad frequency distribution. A suitable measure for the breadth of frequency distribution is the standard deviation. For example, the two illuminating steps can be performed in such automated manner that the illuminating conditions, especially the light intensity of the collimated or diffuse light, vary stepwise over a given area and a gray level histogram is taken for each setting, its frequency distribution is determined and the appertaining standard deviation is calculated. Then, the light intensity by which the utmost standard deviation could have been obtained is set, and an image is taken at this light intensity-and finally analyzed.

Preferably, the mask is generated in such a manner that the unmasked regions are generated in form of a list of the pixels of the image processing means which have to be taken into consideration to set the illuminating conditions in the second illuminating step. Thus, the mask is just a virtual, electronically stored mask. To generate the mask, the gray level values of the image taken in the first illuminating step can be used. As for the definition of relatively dark and relatively bright areas, a threshold value can be determined in advance in the gray level scale. Those image areas whose gray level values are below such threshold value are bright areas and, thus, defined as masked regions, whereas those image areas whose gray level values are above such threshold are dark areas and defined as unmasked regions.

As soon as optimum illuminating conditions could have been obtained by the inventive method for the second illuminating step, an image is taken at the light intensity value detected therefor. Preferably, the mask is used not only to set the optimum illuminating conditions but also to take the image to be analyzed, in order to fade out the areas defined as areas of no defect. For example, according to the electronic list of the pixels not to be taken into consideration, the output of all these pixels is set to zero so that the corresponding areas on the taken image appear as black areas.

In the following, the inventive method is explained in detail by means of a defective paint coating sample, in which.

Figure 1:
FIG. 1 is an image of a defective sample surface taken with collimated light.
Figure 3A:
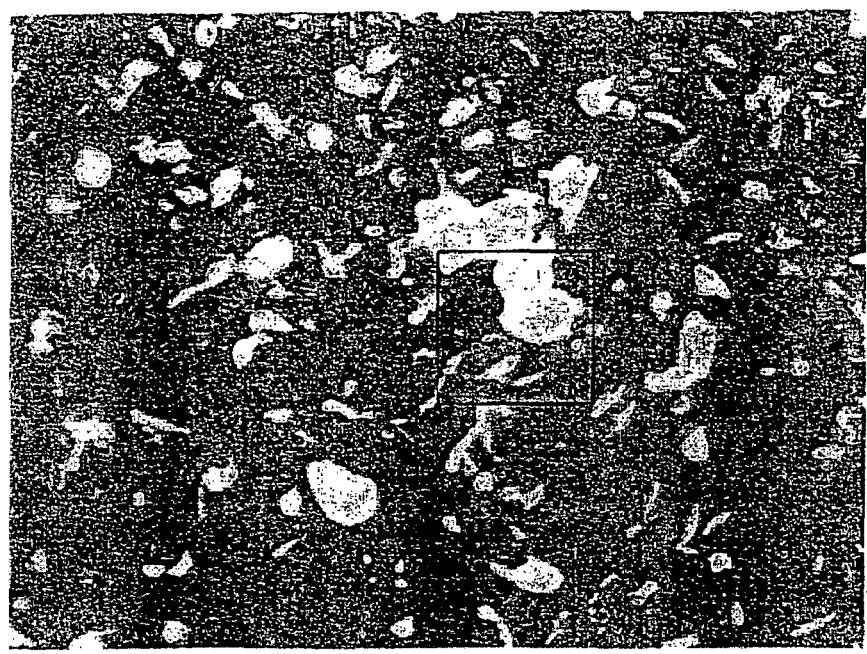
Figure 4A:
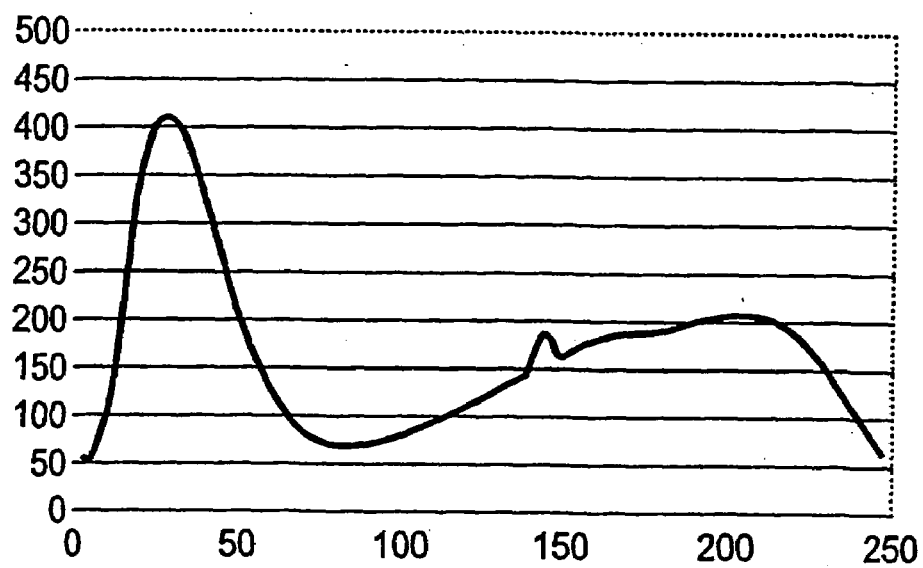

FIG. 3A,B is an image of the masked sample surface according to FIG. 1 taken with diffuse light (A) and an enlarged section of a defective area to make the individual gray level regions thereof visible (B);

FIG. 4A,B are smoothed gray level histograms of the image according to FIG. 3A (B) and of a corresponding image taken without use of the mask (B).

Figure 5:
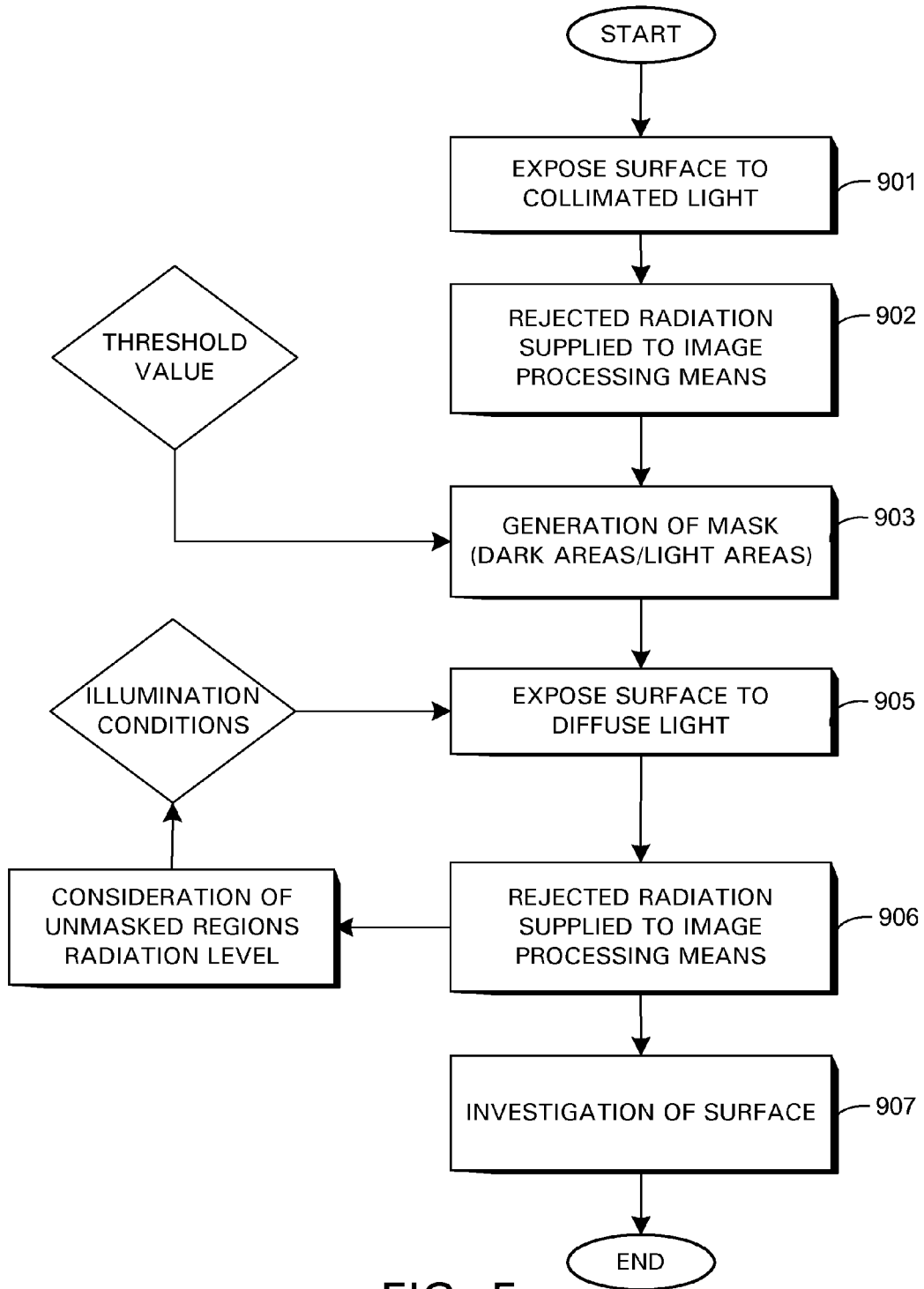

FIG. 5 is a schematic illustration of possible steps of the method to detect and analyze defects of a sample surface.

The images described in the following were taken with a prior art image recognition system known per se by which a sample to be investigated can be illuminated either with collimated or with diffuse light. As concerns the structure of such an equipment it is hereby referred to the above-referenced specification WO 98/16815, particularly FIG. 1 with appertaining description.

FIG. 1 refers to a paint coating sample damaged by splinter bombardment, said image being taken with collimated light. As can be seen, with this kind-of light the damaged areas of the paint coating are substantially black and the undamaged coating areas are white.

The images are taken by means of an electronic video camera provided with a CCD chip as position-resolving detector. The paint coating surface is mapped to the CCD chip. The individual pixels can take gray level values on a scale ranging between 0 and 255. The light intensity is varied in predetermined steps, and for each set light intensity a frequency distribution of the gray level values of the taken image is detected from which the standard deviation will then be detected. Now, the light intensity of utmost standard deviation is selected and the image taken used for further analysis. This image is shown in FIG. 1.

Figure 2:
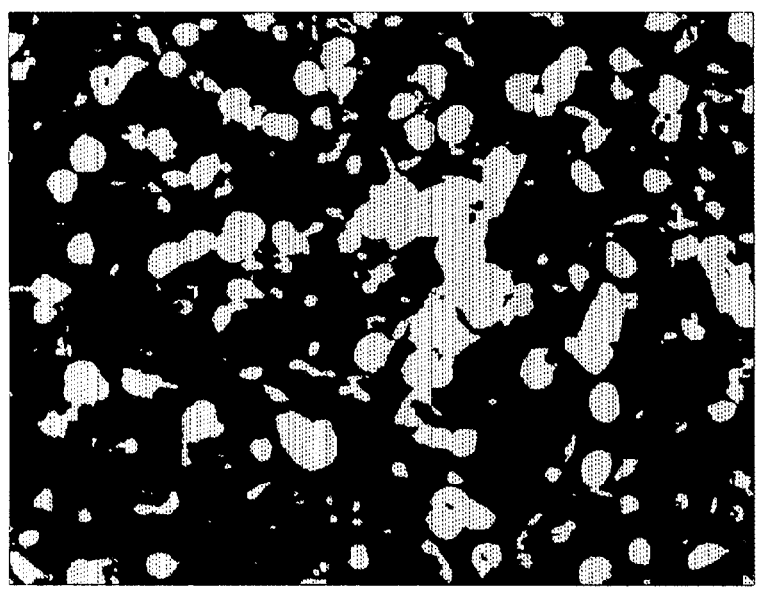
FIG. 2 is a mask generated from the image according to FIG. 1.

Now, the image of FIG. 1 is used to generate a mask, i.e. regions are defined which have to be taken into consideration for further image processing steps, particularly for setting the optimum illuminating conditions when taking an image with diffuse light, as well as those which are no longer considered. According to FIG. 2, the masked regions are black and the unmasked regions are gray.

The black, masked regions are present in form of an electronic list of CCD detector pixels whose gray level value is below a predetermined given threshold value so that they have thus been defined as regions without defects. To generate the mask, the gray level values of the taken picture are, thus, divided into two regions, viz. unmasked defective regions and masked regions without any defects.

Now, an image of the paint coating surface is taken with diffuse light. As in case of the exposure taken with collimated light, the light-intensity of the diffuse light is also varied in given steps and for each set light intensity a frequency distribution of the gray level values of the taken image is detected from which the standard deviation will then be detected. In doing so, however, only the gray level values of those pixels are taken into consideration which correspond to the unmasked regions of the mask generated in the preceding step. Frequency distribution and standard deviation are determined from said gray level values only.

As soon as a given light intensity area has thus been passed, the light intensity of utmost standard deviation of the frequency distribution is then selected and the image taken analyzed. To take the picture, the gray level values of the pixels corresponding to the masked regions can be set to zero so that they appear as black areas, as already shown for the mask according to FIG. 2.

Figure 3B:
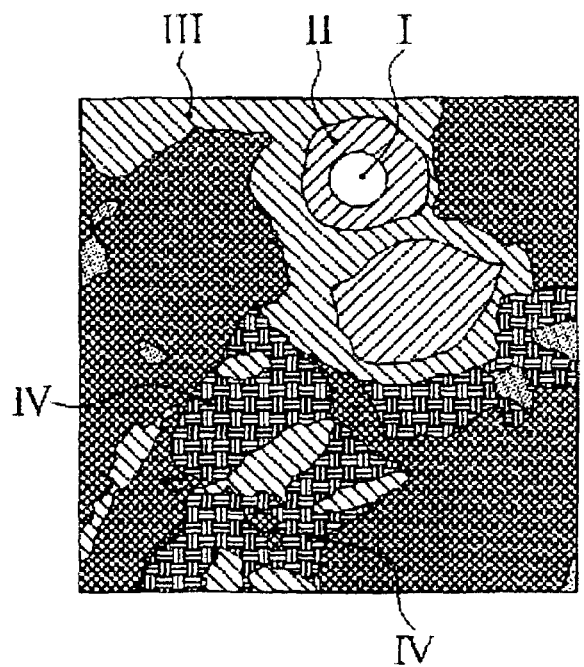

FIG. 3A shows the black-and-white copy of a pseudo-color representation generated from the taken image, wherein different colors have been assigned to certain prevailing image gray level values. The enlarged square section of FIG. 3B shows a region of about the middle of the image. According to said section, the detected defects can be classified into four different groups or types of areas, viz. I-IV.

The upper half of the image refers to a circular area of type I. In this area, the metal of the body has been laid bare by means of splinter bombardment. The areas surrounding said area are of type II and III and hatched.

A circular area of type II surrounds the circular metal area so that it can be assumed that the material of the successively following coat layer has been laid bare in this area. Accordingly, areas of this kind are generated by the first coat layer applied to the metal, i.e. the electrocoat layer. This area is in turn surrounded by a type III-area so that it can be assumed that this is the successively following layer of the coat structure, viz. the filler coat layer which has been laid bare in the areas of type III. The bottom part of the image shows darker areas of type IV which mostly surround areas of type III. Hence follows that the paint coat layer has been laid bare at these locations.

It is not possible to detect any defects in the transparent coat layer such as scratches or the like when the picture was taken with diffuse light but only if it was taken with collimated light. Thus, they can easily be identified due to the fact that certain areas are black when the picture was taken with diffuse light, as such picture only shows defective areas.

Figure 4B:
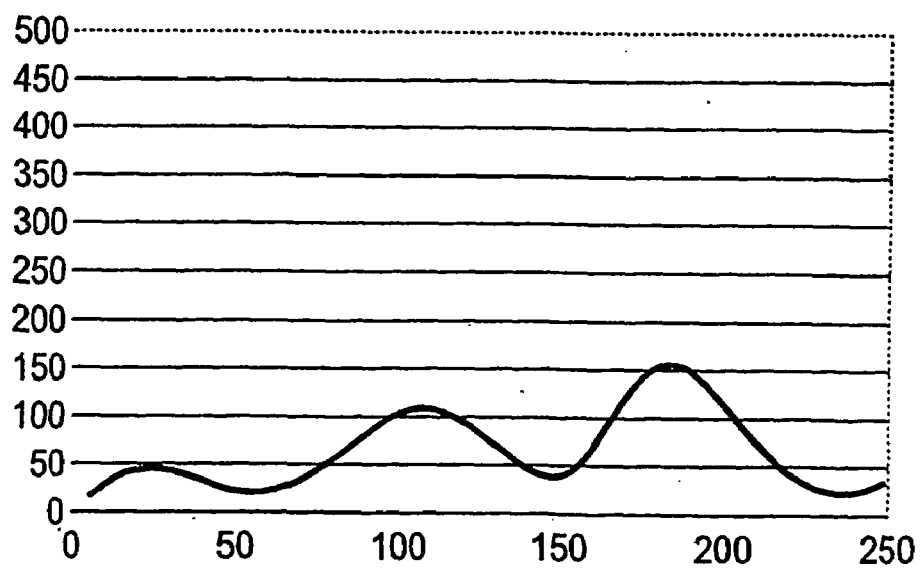

FIG. 4A,B show smoothed gray level histograms, wherein FIG. 4a refers to a gray level histogram of an image of the paint coating sample taken with diffuse light without use of a mask. The influence of bright areas with no defects of low gray level values forming a broad maximum in the left-side half can be clearly seen. In contrast thereto, FIG. 4B shows a gray level histogram generated for the same sample by use of the mask. Without mask, the decisive information in the defective areas is covered so that the contrasts in this area cannot be optimized.

The spherical arrangement used to generate the diffuse light, also referred to as "globe photometer", can also use LEDs as light sources, e.g. red, green and blue LEDs by which the entire color spectrum can be covered and, thus, depending on the requirements and the color of the paint coating of the sample to be investigated, diffuse light of a special color can be directed to the surface of the sample.

The invention claimed is:

1. A method to detect and analyze defects of a sample surface comprising:
   (a) exposing a surface to be investigated to collimated light and supplying radiation rejected therefrom to a position-resolving image processing means;
   (b) generating a mask on the basis of the image supplied by the image processing means, said mask having masked regions being defined by relatively bright areas of said image and unmasked regions being defined by relatively dark areas of said image, wherein a threshold value is determined in the gray level scale and image areas whose gray level values are below such threshold value are relatively bright areas and image areas whose gray level values are above such threshold value are relatively dark areas; and
   (c) exposing the surface to be investigated to diffuse light and supplying radiation rejected therefrom to the image processing means, with only the radiation from the unmasked regions being taken into consideration for setting illuminating conditions.

2. The method as set forth in claim 1, wherein
the image signals obtained by said image processing means during steps (a) and (c) are digitized and gray level histograms of said images are generated by a computer.

3. The method as set forth in claim 2, wherein
the illuminating conditions are set in such a manner that a parameter, particularly the standard deviation, representing the distribution of the gray level values in the gray level, histogram is maximized, and the image generated under said illuminating conditions is selected.

4. The method as set forth in claim 2, wherein
the relatively dark or relatively bright areas are defined in step (b) in that their gray level values are either above or below a predetermined threshold value.

5. The method as set forth in claim 2, wherein
the mask is generated in such a manner that the unmasked areas are generated in the form of a list of pixels of the image processing means that have to be taken into consideration for analyzing purposes.

6. The method as set forth in claim 3, wherein the relatively dark or relatively bright areas are defined in step (b) in that their gray level values are either above or below a predetermined threshold value.

7. The method as set forth in claim 3, wherein the mask is generated in such a manner that the unmasked areas are generated in the form of a list of pixels of the image processing means that have to be taken into consideration for analyzing purposes.

8. The method as set forth in claim 4, wherein the mask is generated in such a manner that the unmasked areas are generated in the form of a list of pixels of the image processing means that have to be taken into consideration for analyzing purposes.

9. The method as set forth in claim 6, wherein the mask is generated in such a manner that the unmasked areas are generated in the form of a list of pixels of the image processing means that have to be taken into consideration for analyzing purposes.

* * * * *